United States Patent
Tamai

(10) Patent No.: US 10,820,612 B2
(45) Date of Patent: Nov. 3, 2020

(54) METHOD FOR PRODUCING FERMENTED BAMBOO EXTRACT AND IMMUNOSTIMULATING AGENT

(71) Applicant: Osamu Tamai, Takamatsu (JP)

(72) Inventor: Osamu Tamai, Takamatsu (JP)

(*) Notice: Subject to any disclaimer, the term of this patent is extended or adjusted under 35 U.S.C. 154(b) by 295 days.

(21) Appl. No.: 15/735,682

(22) PCT Filed: Jun. 13, 2016

(86) PCT No.: PCT/JP2016/067571
§ 371 (c)(1),
(2) Date: Dec. 12, 2017

(87) PCT Pub. No.: WO2016/204120
PCT Pub. Date: Dec. 22, 2016

(65) Prior Publication Data
US 2020/0029610 A1    Jan. 30, 2020

(30) Foreign Application Priority Data

Jun. 15, 2015 (JP) .................. 2015-120180

(51) Int. Cl.
| | |
|---|---|
| *A61K 36/00* | (2006.01) |
| *A23K 20/163* | (2016.01) |
| *A23L 33/105* | (2016.01) |
| *A23P 10/47* | (2016.01) |
| *A61K 36/899* | (2006.01) |
| *A61K 8/9794* | (2017.01) |

(52) U.S. Cl.
CPC .......... *A23K 20/163* (2016.05); *A23L 33/105* (2016.08); *A23P 10/47* (2016.08); *A61K 8/9794* (2017.08); *A61K 36/899* (2013.01); *A61K 2236/19* (2013.01); *A61K 2236/37* (2013.01)

(58) Field of Classification Search
None
See application file for complete search history.

(56) References Cited

FOREIGN PATENT DOCUMENTS

| | | |
|---|---|---|
| CN | 1969682 A | 5/2007 |
| CN | 103265647 A * | 8/2013 |
| JP | 2524944 B2 | 8/1996 |
| JP | 2005-151928 A | 6/2005 |
| JP | 2006-116433 A | 5/2006 |
| JP | 2007-161604 A | 6/2007 |
| JP | 2008-094733 A | 4/2008 |
| JP | 2010-29110 A | 2/2010 |
| JP | 2010029110 A | 2/2010 |
| JP | 2012-162488 A | 8/2012 |
| JP | 5357459 B2 | 12/2013 |
| JP | 2014-64564 A | 4/2014 |
| JP | 2014-64565 A | 4/2014 |
| KR | 10-2006-0019135 A | 3/2006 |
| WO | 2012/108347 A1 | 8/2012 |

OTHER PUBLICATIONS

Notice of Preliminary Rejection dated Nov. 20, 2018, issued in counterpart Korean Application No. 10-2017-7034766. (6 pages).
Extended Search Report dated Nov. 30, 2018. issued in counterpart EP Application No. 16811594.7 (8 pages).
Perdigon et al., "Systemic augmentation of teh immune response in mice by feeding fermented with Lactobacillus casei and Lactobacillus acidophilus ", Immunology, (1988), vol. 63, pp. 17-23. Cited in ISR. (7 pages).
International Search Report dated Jul. 19, 2016, issued in counterpart International Application No. PCT/JP2016/067571 (1 page).
Office Action dated Jul. 16, 2020, issued in counterpart CN Application No. 201680034537.7 (13 pages).

* cited by examiner

*Primary Examiner* — Qiuwen Mi
(74) *Attorney, Agent, or Firm* — Westerman, Hattori, Daniels & Adrian, LLP

(57) ABSTRACT

An object of the present invention is to provide a new application of bamboo based on new functions. A method for producing a fermented bamboo extract comprises a pulverization step of pulverizing bamboo to obtain bamboo powder, a fermentation step of fermenting the bamboo powder with lactic acid bacteria to obtain a fermented bamboo product, and an extraction step of subjecting the fermented bamboo product to hot water extraction to obtain an extract.

6 Claims, 5 Drawing Sheets

METHOD FOR PRODUCING FERMENTED BAMBOO EXTRACT AND IMMUNOSTIMULATING AGENT

TECHNICAL FIELD

The present invention relates to a method for producing a fermented bamboo extract, whereby the fermented bamboo product resulting from lactic fermentation of bamboo is obtained by extraction, and an immunostimulating agent and a food composition for immunostimulation comprising the fermented bamboo extract as an active component.

BACKGROUND ART

Bamboo is a gramineous plant mainly seen in Asian areas including Japan. Bamboo grows fast and can easily be cut over, so that bamboo has been broadly used from old times as construction materials, and materials for craft articles and everyday items. However, the advent of chemical materials such as synthetic resin lowers the use of bamboo materials and causes a problem such that bamboo groves left uncut erode hills, fields and agricultural land. Moreover, even managed bamboo groves are problematic in expensive waste disposal cost because no one takes over the cut bamboo.

Accordingly, in order to effectively utilize bamboo, research and development are being conducted on the new applications of bamboo. For example, Patent Literature 1 discloses that cuticle portions of bamboo materials have antimicrobial properties, and fine bamboo powder obtained from the cuticle portion of a bamboo material is used as a deodorant antimicrobial material. Furthermore, Patent Literature 2 to Patent Literature 4 written by the present inventor disclose lactic fermented bamboo powder obtained by lactic fermentation of bamboo powder resulting from pulverization of bamboo materials, and also disclose that the lactic fermented bamboo powder can be applied to livestock feeds, plant fertilizers, soil conditioners, deodorizing products, antimicrobial products and the like.

CITATION LIST

Patent Literature

Patent Literature 1: Japanese Patent No. 2524944
Patent Literature 2: Japanese Patent No. 5357459
Patent Literature 3: Japanese Patent Laid-Open No. 2014-64564
Patent Literature 4: Japanese Patent Laid-Open No. 2014-64565

SUMMARY OF INVENTION

Technical Problem

Various new bamboo applications as described above have been proposed, and applications based on new functions that enhance the value of bamboo are expected, in order to enhance the further use of bamboo.

The present invention has been conceived in view of the above points, and an object thereof is to provide a new application of bamboo based on new functions.

Furthermore, another object of the present invention is to provide a new application of bamboo based on technology concerning lactic fermented bamboo powder, which has been proposed by the present inventor.

Solution to Problem

The present inventor has discovered that an extract having an immunostimulating action can be obtained by subjecting a fermented bamboo product obtained by fermenting bamboo with lactic acid bacteria to hot water extraction, and thus has completed the present invention. Hence, the method for producing a fermented bamboo extract of the present invention, which addresses the above problems to be solved, comprises a pulverization step of pulverizing bamboo to obtain bamboo powder, a fermentation step of fermenting the bamboo powder with lactic acid bacteria to obtain a fermented bamboo product, and an extraction step of subjecting the fermented bamboo product to hot water extraction to obtain an extract. With the method, a fermented bamboo extract having an immunostimulating action can be easily obtained. Bamboo powder obtained by pulverization of bamboo is used as a raw material for fermentation, so that the surface area with which microorganisms come into contact is increased, as well as saccharides, amino acids, vitamins and the like contained within cells are eluted into bamboo powder as a result of pulverization, lactic acid bacteria having resided in fine honeycomb structure-like parenchyma and the like are also dispersed within bamboo powder, and thus lactic acid bacteria efficiently grow to accelerate fermentation. Furthermore, a fermented bamboo extract having an immunostimulating action is obtained by subjecting the fermented bamboo product to hot water extraction, so that the extract has a high level of safety and is applicable without anxiety to foods, beverages, cosmetics and medicines, as well as various products including livestock feeds, aquaculture additives or agricultural formulations, for example.

Also, the method for producing a fermented bamboo extract of the present invention further comprises preferably a precipitate forming step of adding alcohol to the extract or a concentrated solution thereof to obtain a precipitate. Accordingly, a fermented bamboo extract having an improved immunostimulating action is obtained.

Also, in the above precipitate forming step, the alcohol is preferably added such that the alcohol has a final concentration of 60 wt % to 80 wt %. Therefore, an appropriate concentration of alcohol to be added for the formation of precipitates is selected.

Moreover, in the above extraction step, hot water extraction is preferably performed on a fermented bamboo product under conditions of 80° C. to 130° C. and 0.1 MPa to 0.3 MPa. Therefore, appropriate temperature and pressure conditions are selected for hot water extraction.

Also, bamboo in the method for producing a fermented bamboo extract of the present invention is preferably a bamboo stem. The use of bamboo stems alone for fermentation materials results in active microbial growth and accelerated fermentation. The use of bamboo stems also facilitates moisture control for fermentation, and thus stabilizes the fermentation state.

Also, the food composition for immunostimulation of the present invention comprises a fermented bamboo extract obtained by the above steps as an active component. The food composition for immunostimulation of the present invention has the action of activating particularly innate immune functions, and thus can activate and enhance innate immune functions, specifically actions such as rapid protection against infection with viruses, bacteria or the like and attacks against malignant tumors via the gut immune mechanism, through ingestion thereof as a food.

Moreover, the immunostimulating agent of the present invention comprises, as an active component, a fermented bamboo extract obtained through steps, in this order, of a pulverization step of pulverizing bamboo to obtain bamboo powder, a fermentation step of fermenting the bamboo powder with lactic acid bacteria to obtain a fermented bamboo product, an extraction step of subjecting the fermented bamboo product to hot water extraction to obtain an extract, and a precipitate forming step of adding alcohol to the extract or a concentrated solution thereof to obtain a precipitate. The immunostimulating agent of the present invention has the action of activating, particularly innate immune functions. Thereby, the immunostimulating agent can activate and enhance innate immune functions of organisms, specifically actions such as rapid protection against infection with viruses, bacteria or the like and attacks against malignant tumors.

Also, the method for producing a fermented bamboo extract of the present invention preferably comprises, in the above fermentation step, adding a culture product containing at least lactic acid bacteria of the genus *Weissella*. Therefore, microbial species appropriate for obtaining a fermented bamboo extract of the present invention is added as a starter, so that less time is required for the fermentation step.

Also, the method for producing a fermented bamboo extract of the present invention comprises, prior to the above fermentation step, a starter bacterium provision step of obtaining a fermented bamboo product by fermenting bamboo powder with lactic acid bacteria, wherein in the fermentation step, it is also preferred to add the fermented bamboo product obtained in the starter bacterium provision step. Therefore, a fermenting microorganism that is habituated to fermentation of bamboo powder is added as a starter, so that less time is required for the fermentation step.

Advantageous Effects of Invention

According to the present invention, a method for producing a fermented bamboo extract, an immunostimulating agent, and a food composition for immunostimulation, which have the following excellent effects, can be provided.
(1) The fermented bamboo extract, the immunostimulating agent and the food composition of the present invention have an immunostimulating action, particularly the action of activating innate immune functions. They also have the action of inducing IL-12 and IFN-γ production, so that they also have a preventive effect against infection with viruses or bacteria, the effect of improving compromised immune functions, and anti-tumor effects, for example.
(2) A raw material to be used is bamboo, and extraction is performed using water or alcohol, so that the fermented bamboo extract, the immunostimulating agent and the food composition of the present invention have a high level of safety, and thus are applicable without anxiety to various products such as foods, functional foods, beverages, cosmetics, pharmaceutical products, livestock feeds, aquaculture additives or agricultural formulations.
(3) The fermented bamboo extract, the immunostimulating agent and the food composition of the present invention can be obtained by fermenting bamboo with lactic acid bacteria, followed by hot water extraction, and thus can be relatively simply produced.
(4) The fermented bamboo extract, the immunostimulating agent and the food composition of the present invention can contribute to the efficient utilization of bamboo materials.

DESCRIPTION OF EMBODIMENTS

First, the method for producing a fermented bamboo extract according to the first embodiment of the present invention is explained with reference to FIG. 1.

Figure 1:
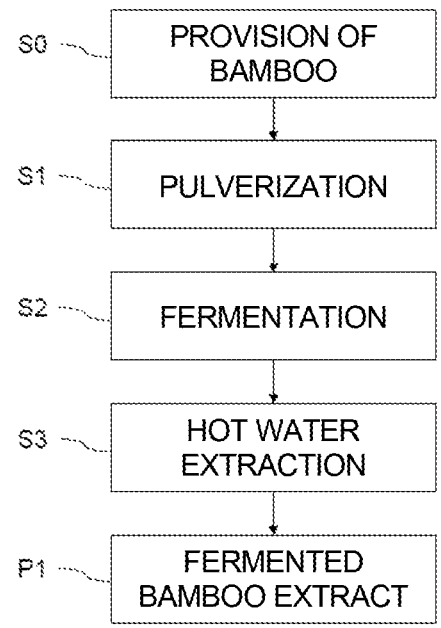
FIG. 1 is a flow chart schematically showing a method for producing a fermented bamboo extract according to a first embodiment of the present invention.

As shown in FIG. 1, the method for producing a fermented bamboo extract P1 of the present invention comprises, briefly, step S0 of providing bamboo as a raw material, pulverization step S1 of pulverizing the bamboo to obtain bamboo powder, fermentation step S2 of fermenting the bamboo powder to obtain a fermented bamboo product, and hot water extraction step S3 of subjecting the fermented bamboo product to hot water extraction.
(Provision of Bamboo)

First, step S0 of providing bamboo shown in FIG. 1 is explained. Examples of bamboo to be used as a raw material for the fermented bamboo extract according to the present invention include wide-ranging gramineous plants generally referred to as bamboo and bamboo grass. Specific examples thereof include, but are not particularly limited to, moso bamboo (*Phyllostachys heterocycla* f. *pubescence*), long-jointed bamboo (*Phyllostachys bambusoides*), henon bamboo (*Phyllostachys nigra*), square-stem bamboo (*Tetragonocalamus quadrangularis*), simon bamboo (*Pleioblastus Simonii*), arrow bamboo (*Pseudosasa japonica*) and kuma bamboo grass (*Sasa veitchii*). Moso bamboo is suitably used. Bamboo can be used intact as raw bamboo, so that cut bamboo can be directly used for the fermented bamboo extract of the present invention without any pretreatment and the like, except for washing off soil and the like attached to bamboo. Raw bamboo is pulverized into powder or cut into chips, so that lactic acid bacteria existing within bamboo stems particularly within fine honeycomb parenchyma are exposed and dispersed, and then fermentation is proceeded by bamboo-derived lactic acid bacteria. Leaves such as leaves of bamboo grass from among bamboo plants are rich in antimicrobial substances, and likely inhibit lactic acid bacterial fermentation in fermentation step S2 described later. Hence, preferably leaves are cut off and only the stems are used in the following steps.
(Pulverization)

Next, pulverization step S1 of pulverizing bamboo is explained. A method for pulverizing bamboo may be any method, as long as bamboo can be pulverized and is not particularly limited. For example, a bamboo pulverizer provided with a rotary blade that is activated when an end face of a raw bamboo tube(s) comes into contact with the blade can be used. With a bamboo pulverizer of this type, a raw bamboo tube is continuously cut in the direction approximately parallel to the raw bamboo tube end face to thereby pulverize the raw bamboo into bamboo powder of a predetermined size. Bamboo is pulverized in a manner such that raw bamboo tube end faces are scraped off by a rotary blade, so that many lactic acid bacteria existing in parenchyma or bundle sheaths of the bamboo stem are exposed to accelerate fermentation in the following fermentation step S2. Moreover, bamboo is pulverized, so that cell walls are disrupted and saccharides such as glucose, amino acids, and vitamins contained in cells are also dispersed within powder, and thus the nutritional requirements of lactic acid bacteria are satisfied and fermentation proceeds efficiently in fermentation step S2.

The particle size of the bamboo powder is not particularly limited. Since excessively fine particle size makes handling difficult, and excessively large particle size lowers the fermentation speed, the particle size is preferably about 50 μm to 1 mm, and more preferably 200 μm to 600 μm. Furthermore, bamboo powder obtained by pulverization is preferably introduced into a metal removal apparatus to remove by adsorption the foreign matter resulting from a rotary blade with a nicked edge of a bamboo pulverizer, for example. Moreover, bamboo powder obtained by pulverization may be introduced into a sieve apparatus, thereby making the particle size ranges of the thus obtained bamboo powder equal, or removing unscraped pieces left unpulverized in pulverization step S1.

(Fermentation)

Next, fermentation step S2 is explained. Bamboo powder is fermented by bamboo-derived lactic acid bacteria. Specifically, for example, bamboo powder obtained by the above pulverization step S1 is packaged in a fermentation vessel, such as a fermentation bag (e.g., transparent resin bag) in a predetermined amount, air within the fermentation bag is removed as much as possible, the opening of the fermentation bag is sealed to make the vessel interior in an almost anaerobic state. The fermentation bag is covered with a lightproof sheet such as a mat, and then left to stand for about 5 to 20 days under an environment at 20° C. to 30° C., so that a lactic fermented product of bamboo powder can be obtained. Fermentation state can be known based on the pH of the bamboo powder. Specifically, lactic acid is generated in bamboo powder as lactic fermentation proceeds, and then the bamboo powder presents acidic pH. After bamboo powder (40 g) is added to 100 mL of purified water, the solution is stirred for 5 minutes and then left to stand for 2 minutes. When the pH of a filtrate obtained by filtration with filter paper is 4.3 or less, this is determined to indicate the sufficient progression of fermentation, and thus fermentation step S2 can be completed.

The fermented bamboo product obtained in fermentation step S2 was subjected to microbiota analysis by denaturing gradient gel electrophoresis (DGGE method). As a result, it was confirmed that at the initial fermentation stage, lactic acid bacteria of the genus *Leuconostoc* and the genus *Weissella* were mainly observed, and, in the case of fermented bamboo product after the completion of fermentation, lactic acid bacteria of the genus *Weissella* dominated the microbiota. Based on the results, a culture product containing lactic acid bacteria of the genus *Weissella* is preferably used as a starter in fermentation step S2. Accordingly, lactic acid bacteria of the genus *Weissella* are used as the dominant species of the microbiota in bamboo powder to quickly accelerate fermentation, so that days for fermentation in fermentation step S2 can be reduced by about 30% to about 3 to 15 days. Moreover, microbiota or microbial count changes depending on temperature fluctuation, and water content, types and the like of bamboo, however, a stable fermented bamboo product can be obtained year-round through the use of such a starter. Regarding the starter, a starter containing lactic acid bacteria of the genus *Weissella* separately cultured in liquid medium is preferably added at 0.5 mL to 5 mL per kg of bamboo powder.

Also, in fermentation step S2, a fermented bamboo product obtained by fermenting bamboo powder in advance is also preferably used as a starter. As described above, a starter bacterium provision step is provided in advance, and then the thus obtained fermented bamboo product is used as a starter, so that the genus *Weissella* as the dominant species contained in the fermented bamboo product accelerates the fermentation of new bamboo powder immediately after pulverization step S1, and days for fermentation in fermentation step S2 can be reduced by about 30% to about 3 to 15 days. Furthermore, the use of such a starter enables to obtain a stable fermented bamboo product independent of climate or bamboo conditions. When a fermented bamboo product provided in advance is used as a starter in this manner, the product is preferably added at 5 g to 20 g per kg of new bamboo powder. Furthermore, it is also effective to use a portion of a fermented bamboo product obtained in this fermentation step S2 as a starter for a next fermentation step.

Also, fermentation in fermentation step S2 is preferably performed under low or medium vacuum conditions, or under an inert gas atmosphere such as nitrogen gas. This inhibits the growth of yeast such as *Hansenula* or *Pichia* in bamboo powder, enabling prevention of the generation of ethyl acetate from acetic acid and ethanol generated by yeast.

(Hot Water Extraction)

Next, hot water extraction step S3 is explained. In hot water extraction step S3, a fermented bamboo product obtained in fermentation step S2 is subjected to hot water extraction to obtain a fermented bamboo extract P1. Examples of a method for hot water extraction include reflux heat extraction and pressurized hot water extraction using an autoclave apparatus or the like. Specifically, for example, a fermented bamboo product and water are added into a reaction reservoir, and then subjected to reflux heating or the like for a predetermined time to extract a fermented bamboo extract. Water is preferably added in an amount of 4 to 15 liters and more preferably 4 to 10 liters per kg of a fermented bamboo product. Water is used as an extraction solvent, and another component can also be contained, as long as it does not hinder the extraction efficiency, and does not affect the action of the thus obtained fermented bamboo extract. Temperature for extraction is preferably 80° C. or higher, more preferably 80° C. to 130° C., and particularly preferably 100° C. to 121° C. Extraction is performed under atmospheric pressure or under pressurization. Pressure of pressurization conditions is preferably 0.1 MPa to 0.5 MPa, and more preferably 0.1 MPa to 0.3 MPa. Time for extraction is preferably 10 minutes to 5 hours, and more preferably 20 minutes to 2 hours. After hot water extraction, a fermented bamboo extract P1 is obtained by removing the residue. Examples of the fermented bamboo extract P1 of the present invention include, a fermented bamboo extract P1 itself obtained in hot water extraction step S3, a concentrated solution obtained by concentrating the fermented bamboo extract P1 by vacuum concentration or the like, and a solid and/or powdery product obtained by subjecting the fermented bamboo extract P1 to dry treatment such as freeze drying.

Next, the method for producing a fermented bamboo extract according to the second embodiment of the present invention is explained with reference to FIG. 2.

Figure 2:
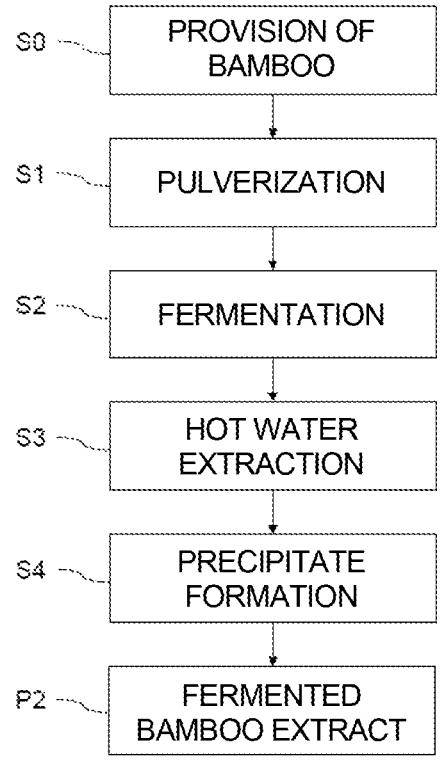
FIG. 2 is a flow chart schematically showing a method for producing a fermented bamboo extract according to a second embodiment of the present invention.

As shown in FIG. 2, the method for producing a fermented bamboo extract P2 of the present invention comprises, briefly, step S0 of providing bamboo as a raw material, pulverization step S1 of pulverizing the bamboo to obtain bamboo powder, fermentation step S2 of fermenting the bamboo powder to obtain a fermented bamboo product, extraction step S3 of subjecting the fermented bamboo product to hot water extraction, and precipitate forming step S4 of obtaining a precipitate from the hot water extract. Of these steps S0 to S4, bamboo provision step S0, pulverization step S1, fermentation step S2 and hot water extraction step S3 are similar to steps S0 to S3 in the above first embodiment, respectively, and the operation and effects thereof are the same. Hence, explanation for these steps is omitted.

(Formation of Precipitate)

Precipitate forming step S4 is explained. Precipitate forming step S4 involves adding alcohol to an extract obtained in hot water extraction step S3 to form a precipitate, and then collecting the precipitate to obtain a fermented bamboo extract P2. Examples of alcohol to be used herein include ethanol and isopropanol, and ethanol is preferred in view of good safety. Alcohol may be added in an amount and a concentration such that a precipitate insoluble in the extract is formed. In view of accelerating efficient formation of precipitate, specifically, alcohol is added such that the alcohol has a final concentration of preferably 50 wt % to 85 wt %, more preferably 60 wt % to 80 wt %, and particularly preferably 65 wt % to 75 wt % in a mixed solution of the extract and alcohol. Moreover, in view of being able to reduce the amount of alcohol to be added into an extract, the extract is preferably subjected to vacuum concentration or the like before the addition of alcohol to obtain a concentrated solution. In this case, the concentration factor for an extract differs depending on the amount of water to be added to a fermented bamboo product in hot water extraction step S3, and an extract is preferably concentrated 3 to 20 times, and more preferably concentrated 5 to 15 times. Alcohol is added in a predetermined amount to a hot water extract or a concentrated solution thereof, so that a component having an immunostimulating action contained in the extract selectively forms a precipitate, disused components are removed, and then a purified fermented bamboo extract P2 is obtained. The obtained precipitate, that is, the fermented bamboo extract P2 is collected by liquid-solid separation such as filtration or centrifugation. The fermented bamboo extract P2 is subsequently dried and then stored as a solid and/or powdery product.

The fermented bamboo extract of the present invention has an immunostimulating action. The term "immunostimulating action" in the present invention refers to the action of improving both functions, natural immunity and acquired immunity. An immunostimulating agent comprising the fermented bamboo extract according to the present invention as an active component has particularly the action of activating innate immune functions, and has the action of inducing IL-12 and IFN-γ production. Thus, innate immune functions, specifically such as rapid protection against infection with pathogens and attacks against malignant tumors can be activated and enhanced. Furthermore, the immunostimulating agent also has the action of activating immunoreaction when immune functions are lowered due to causes such as aging, stress and fatigue, or the action of stably maintaining immune functions even when exposed to causes such as aging, stress and fatigue. Moreover, the fermented bamboo extract of the present invention has the action of inducing IL-12 and IFN-γ production, and thus the extract is expected to have the action of not only activating Th1 cells to enhance cell-mediated immunity, but also suppressing humoral immunity through enhanced cell-mediated immunity to suppress allergic reaction.

The immunostimulating agent of the present invention can be used for foods, beverages, cosmetics, quasi drugs and pharmaceutical products, as well as various products including livestock feeds, aquaculture additives or agricultural formulations, for example. The fermented bamboo extract serving as an active component results from the discovery of new functions of bamboo such as young bamboo shoots that have been used for foods, has a high level of safety, and can be ingested daily. Therefore, the fermented bamboo extract is preferably used as a composition for foods or beverages. A food composition for immunostimulation comprising the fermented bamboo extract as an active component can be used in all forms including forms of supplements such as tablets, encapsulated formulations, granules and syrups, beverages, sweets, bread, rice gruel, cereals, noodles, jelly, soup, dairy products, flavoring agents, and edible oil. Also, when used as a food composition, other active components, vitamins, and nutrients such as minerals or amino acids can also be used in various combinations, as long as they do not affect the efficacy of the active component of the present invention. Examples of foods developed from the food composition of the present invention include supplements, health foods, functional foods, and foods for specified health uses. The food composition can also be used for non-human animals (e.g., pet, livestock and aquaculture animal), and in this case can be used in the form of a feed, a pet food, an animal supplement, an animal beverage or the like.

When the immunostimulating agent of the present invention is used as a pharmaceutical product or a quasi drug, the agent can be prepared into various forms by conventionally employed methods. In this case, the immunostimulating agent can be formulated using a pharmacologically acceptable carrier, diluent, lubricating agent, dispersing agent, disintegrating agent, buffering agent, solvent, extending agent, preservative, flavoring agent, stabilizing agent or the like for general formulations, and an excipient acceptable as an excipient for pharmaceutical products. Furthermore, in order to improve bioavailability and stability, a drug delivery system involving a formulation technique such as inclusion using microcapsule, liposomal formulation, fine pulverization, cyclodextrin or the like can also be used. Examples of a dosage form can include, but are not particularly limited to, tablets, granules, encapsulated formulations and syrups.

Regarding a pharmaceutical product, a food composition or the like comprising the immunostimulating agent of the present invention, the daily intake of the fermented bamboo extract is preferably 1 mg to 10 g, and more preferably 1 mg to 1 g in terms of dry weight.

Examples of the present invention are described below, but the present invention is not limited to these Examples.

EXAMPLES

Example 1

1. Production of Fermented Bamboo Extract (1)

Moso bamboo with a stem height of about 4 m was cut over, leaves were cut away with a hatchet to leave stems alone, and then the stems were washed with water to remove soil, dirt and the like. These Moso bamboo stems with a length of about 4 m were pulverized using a bamboo pulverizer (product of Marudai Ironworks Co., Ltd., model: PA-Z), thereby obtaining about 10 kg of the bamboo powder with a size of 500 μm or less. Next, 10 kg of pulverized bamboo powder was added into a resin bag with a capacity of 15 kg, the outer edge of the resin bag was pressed to remove air within the bag as much as possible, and then the opening was sealed. The resin bag was covered with a lightproof sheet, and then left to stand under an environment at 25° C. for 14 days. After 14 days, a portion of the fermented bamboo product was taken and then subjected to microbiota analysis by denaturing gradient gel electrophoresis (DGGE method). Lactic acid bacteria of the genus *Weissella* (*Weissella cibaria* or *confusa*) were confirmed to dominate the microbiota. The thus obtained fermented bamboo product (1 kg) was added into a reaction reservoir for reflux heating, 5 L of water was poured, and then hot water extraction was performed by heating under reflux. The reaction time was set to 60 minutes. After the completion of reaction, a mixture within the reaction reservoir was filtered to collect a filtrate (about 4.5 L) as an extract. A 15% aqueous ethanol solution (6 L) was added to 4.5 L of the extract, the resulting insoluble component was precipitated, and thus a precipitate was collected. The collected precipitate was freeze-dried, so that about 30 g of a fermented bamboo extract (1) was obtained.

Example 2

2. Production of Fermented Bamboo Extract (2)

Moso bamboo with a stem height of about 4 m was cut over, leaves were cut away with a hatchet to leave stems alone, and then the stems were washed with water to remove soil, dirt and the like. These Moso bamboo stems with a length of about 4 m were pulverized using a bamboo pulverizer (product of Marudai Ironworks Co., Ltd., model: PA-Z), thereby obtaining about 10 kg of bamboo powder with a size of 500 μm or less. The fermented bamboo product (100 g) obtained in Example 1 was added to and mixed well with 10 kg of the bamboo powder. Next, the bamboo powder was added into a resin bag with a capacity of 15 kg, the outer edge of the resin bag was pressed to remove air within the bag as much as possible, and then the opening was sealed. The resin bag was covered with a lightproof sheet, and then left to stand under an environment at 25° C. for 9 days. The thus obtained fermented bamboo product (1 kg) was added into a reaction reservoir for reflux heating, 5 L of water was poured, and then hot water extraction was performed by heating under reflux. The reaction time was set to 60 minutes. After the completion of reaction, a mixture within the reaction reservoir was filtered to collect a filtrate (about 4.5 L) as an extract. A 15% aqueous ethanol solution (6 L) was added to 4.5 L of the extract, the resulting insoluble component was precipitated, and thus a precipitate was collected. The collected precipitate was freeze-dried, so that about 30 g of a fermented bamboo extract (2) was obtained.

Example 3

3. Production of Fermented Bamboo Extract (3) for Immune Functional Activity Test The fermented bamboo product obtained in Example 1 was suspended in sterile physiological saline (0.9% NaCl) to give a sample concentration of 100 mg/mL. The suspended matter was treated in an autoclave at 121° C. for 20 minutes to perform hot water extraction of the fermented bamboo product. The hot water extract was centrifuged to collect a supernatant, thereby obtaining a fermented bamboo extract (3). The supernatant was used for an immune stimulation test. Further, 1 mL of the collected supernatant was evaporated to dryness using a centrifugal evaporator, and then the concentration of the fermented bamboo extract (3) in the supernatant was calculated based on the obtained dry weight.

Example 4

4. Production of Fermented Bamboo Extract (4) for Immune Functional Activity Test The fermented bamboo product obtained in Example 2 was suspended in sterile physiological saline (0.9% NaCl) to give a sample concentration of 100 mg/mL. The suspended matter was treated in an autoclave at 121° C. for 20 minutes to perform hot water extraction of the fermented bamboo product. The hot water extract was centrifuged to collect a supernatant, thereby obtaining a fermented bamboo extract (4). The supernatant was used for an immune stimulation test. Further, 1 mL of the collected supernatant was evaporated to dryness using a centrifugal evaporator, and then the concentration of the fermented bamboo extract (4) in the supernatant was calculated based on the obtained dry weight.

Example 5

5. Immune Functional Activity Test

As an immune functional activity test, a natural immunity-accelerating activity test was conducted using silkworm muscle contraction as an indicator. Specifically, this test method is based on findings such that when a test sample is administered to holometabola larvae such as silkworm, sudden muscle contraction takes place if a neurotransmitter is present in the test sample, however, when a substance having the action of activating innate immune functions is administered to holometabola larvae, slow muscle contraction (slowly-progressive muscle contraction) taking about 10 minutes to complete takes place. A test was conducted as follows using the fermented bamboo extract (3) obtained in Example 3 and the fermented bamboo extract (4) obtained in Example 4 as test samples.

Figure 3A:
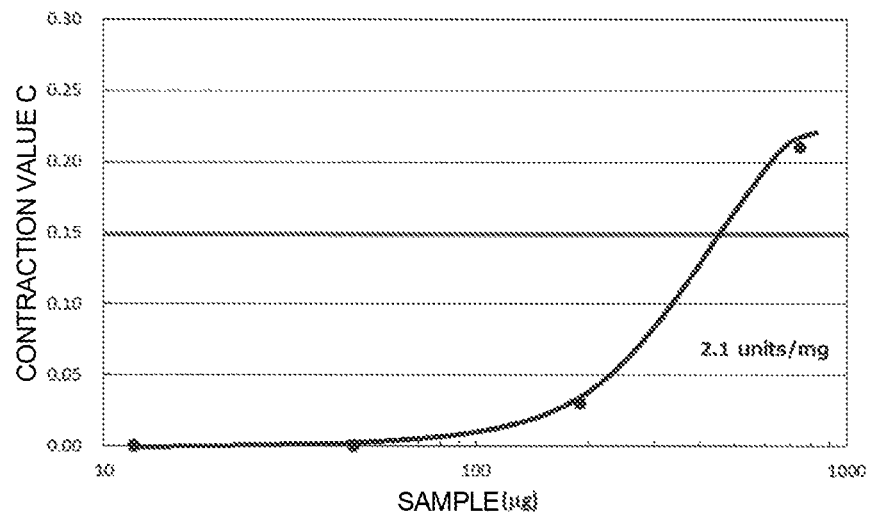
FIGS. 3A and 3B show graphs showing the results of measuring the immune functional activity of fermented bamboo extracts of the present invention in Example 5.
Figure 3B:
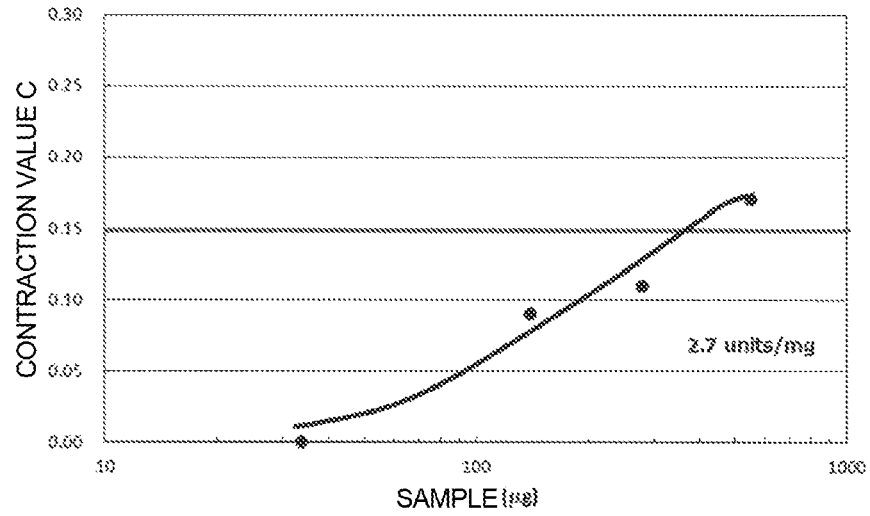

The slowly-progressive muscle contraction of silkworm was measured as follows (see Hamamoto H., Kamimura M., Sekimizu K., J. Biol. Chem., 2008, 283(4), pp. 2185-91). A test sample (50 μL) was intracoelomically injected into a decapitated muscle specimen of a 5-day-old silkworm, the body length of the silkworm was measured, and then the maximum value of the muscle contraction value (Contraction Value, C value=([length before contraction (before injection)]−[length after contraction (after injection)])/[length before contraction]) (about 10 minutes later) was found. Test samples were diluted by serial dilution to predetermined concentrations with 0.9% physiological saline as shown in Table 1 below. C value was measured for each diluent. The slowly-progressive muscle contraction activity in the case of C value=0.15 was defined as 1 unit, the amount of each test sample that gives C value=0.15 was found from the thus obtained dose-response curve, and thus activity per mg of the test sample was calculated. Moreover, 50 μL of physiological saline was used as a negative control, and 0.2 mL of air was used as a positive control. The results are shown in Table 1 below and FIG. 2. FIG. 3(a) shows the result of the fermented bamboo extract (3), and FIG. 3(b) shows the result of the fermented bamboo extract (4).

TABLE 1

| Test sample (Example) | Dilution ratio | Contraction value (C value) | Amount of test sample (μg) |
|---|---|---|---|
| Negative control (0.9% NaCl) | — | 0.00 | — |
| Positive control (air) | — | 0.41 | — |
| Fermented bamboo extract (3) (concentration: 15 mg/mL) | 1/1 | 0.21 | 750 |
|  | 1/4 | 0.03 | 190 |
|  | 1/16 | 0.00 | 47 |
|  | 1/64 | 0.00 | 12 |
| Fermented bamboo extract (4) (concentration: 11 mg/mL) | 1/1 | 0.17 | 550 |
|  | 1/2 | 0.11 | 280 |
|  | 1/4 | 0.09 | 140 |
|  | 1/16 | 0.00 | 34 |

Comparative Example 1

6. Production of Lactic Fermented Bamboo Solution for Immune Functional Activity Test and Immune Functional Activity Test The fermented bamboo product (1 kg) obtained in Example 1 was added into a plastic vessel with a capacity of 10 L, 20 g of bamboo charcoal powder and 6 g of papain enzyme were added and then the mixture was mixed well. Furthermore, 8 L of water was poured, a lid was put on the vessel, and then the resultant was left to stand under an environment at 25° C. for 14 days. After 14 days, the mixture within the vessel was filtered to collect a filtrate (about 8 L) as a lactic fermented bamboo solution. Ten (10) mL of the lactic fermented bamboo solution was taken, the pH was measured with pH test paper and then neutralized with NaOH. Furthermore, 1 mL of the lactic fermented bamboo solution was evaporated to dryness using a centrifugal evaporator, and then the concentration of a component contained in the lactic fermented bamboo solution was calculated based on the thus obtained dry weight. An immune functional activity test similar to that in Example 5 was conducted using the lactic fermented bamboo solution as a test sample. The results are shown in Table 2 below and FIG. 4.

TABLE 2

| Test sample (Comparative Example) | Dilution ratio | Contraction value (C value) | Amount of test sample (μg) |
|---|---|---|---|
| Negative control (0.9% NaCl) | — | 0.00 | — |
| Positive control (air) | — | 0.41 | — |
| Lactic fermented bamboo solution (concentration: 16 mg/mL) | 1/1 | 0.01 | 800 |
|  | 1/4 | 0.00 | 200 |
|  | 1/16 | 0.04 | 50 |

Figure 4:
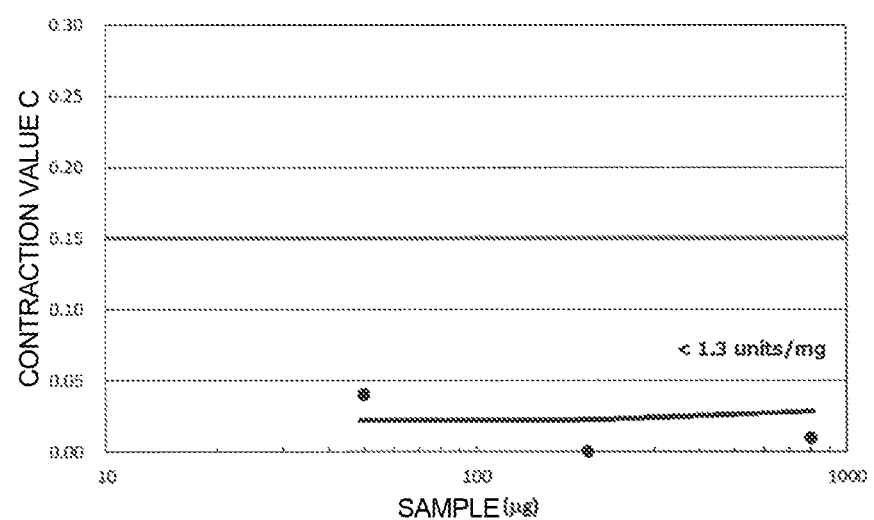
FIG. 4 is a graph showing the result of measuring the immune functional activity of a lactic fermented bamboo solution in Comparative Example 1.

As shown in Table 1, the concentration of the fermented bamboo extract (3) was 15 mg/mL, and the concentration of the fermented bamboo extract (4) was 11 mg/mL. Furthermore, the immune functional activities of these extracts were measured. Dose-response curves were observed as shown in FIG. 3, revealing that the fermented bamboo extracts of the present invention had activity of accelerating natural immunity. The specific activity of the fermented bamboo extract (3) was 2.1 units/mg, and the specific activity of the fermented bamboo extract (4) was 2.7 units/mg. On the other hand, in the case of the lactic fermented bamboo solution described in the Comparative Example, no dose-response curve was observed as shown in FIG. 4, and no activity of accelerating natural immunity was observed. It was revealed by these results that a fermented bamboo extract obtained by subjecting a fermented bamboo product to hot water extraction has an immunostimulating action.

Example 6

7. Production of Fermented Bamboo Extract (5)

The fermented bamboo product (10 g) obtained in Example 1 was suspended in 100 mL of sterile physiological saline (0.9% NaCl). The suspended matter was treated in an autoclave at 121° C. under an atmospheric pressure of 2 for 20 minutes to perform hot water extraction of the fermented bamboo product. The hot water extract was centrifuged to collect a supernatant and then evaporated to dryness using a centrifugal evaporator, so that 440 mg of a powdery fermented bamboo extract (5) was obtained. Furthermore, the amount of saccharides contained in the thus obtained fermented bamboo extract (5) was quantified by a phenol sulfuric acid method. Hence, saccharides were found to account for 7 wt % of the fermented bamboo extract (5) (see Table 4).

Example 7

8. Production of Fermented Bamboo Extract (6)

The fermented bamboo product (10 g) obtained in Example 1 was suspended in 100 mL of sterile physiological saline (0.9% NaCl). The suspended matter was treated in an autoclave at 121° C. under an atmospheric pressure of 2 for 20 minutes to perform hot water extraction of the fermented bamboo product. The hot water extract was centrifuged to collect a supernatant. To the collected supernatant, 95% ethanol was added. Ethanol was added until the ethanol reached a final concentration of 68%. The formed precipitate was collected and then dried, thereby obtaining 27 mg of a powdery fermented bamboo extract (6). Furthermore, the amount of saccharides contained in the obtained fermented bamboo extract (6) was quantified by a phenol sulfuric acid method. Hence, saccharides were found to account for 52 wt % of the fermented bamboo extract (6) (see Table 4).

Example 8

9. Immune Functional Activity Test for Fermented Bamboo Extracts (5) and (6)

Figure 5A:
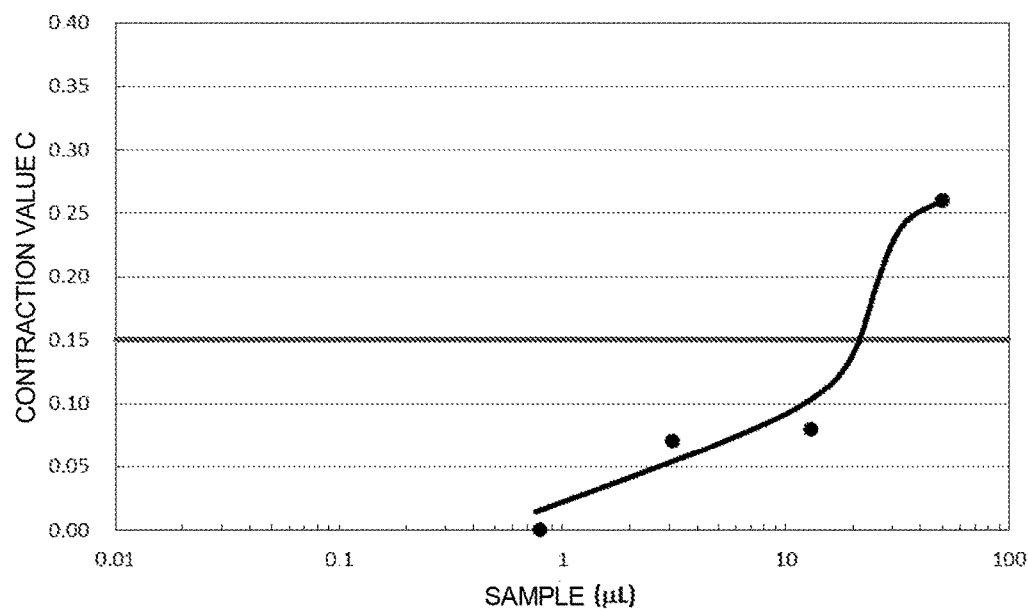
FIGS. 5A and 5B show graphs showing the results of measuring the immune functional activity of fermented bamboo extracts in Example 8.
Figure 5B:
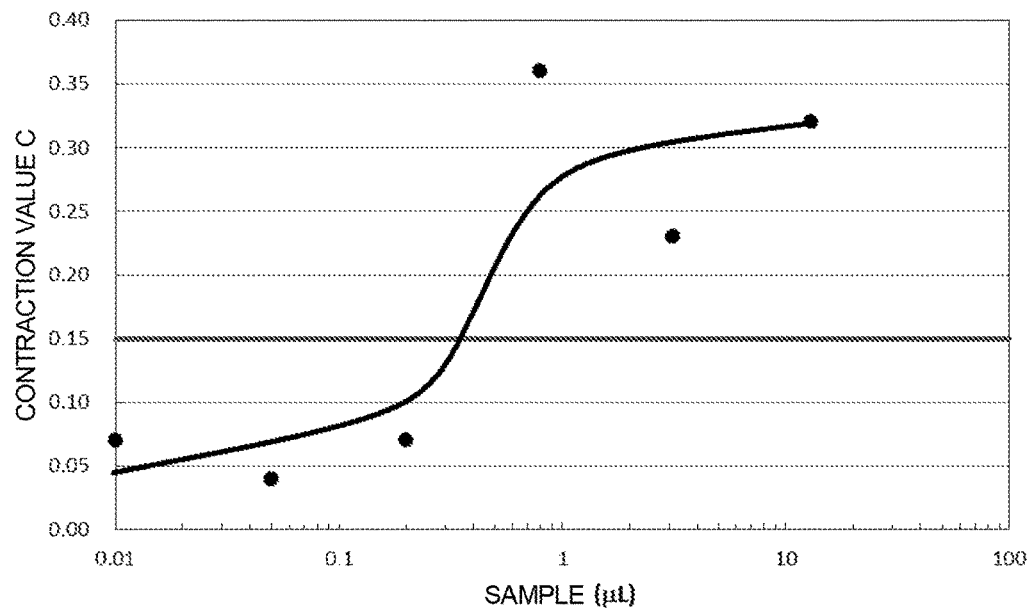

An immune functional activity test was conducted by a method similar to that in Example 5 using the fermented bamboo extract (5) and the fermented bamboo extract (6) obtained in Example 7 and Example 8 as test samples. The results are shown in Table 3 below and FIG. 5. FIG. 5(a) shows the result of the fermented bamboo extract (5) and FIG. 5(b) shows the result of the fermented bamboo extract (6).

TABLE 3

| Test sample (Example) | Dilution ratio | Contraction value (C value) |
|---|---|---|
| Negative control (0.9% NaCl) | — | 0.00 |
| Positive control (air) | — | 0.35 |
| Fermented bamboo extract (5) (autoclaved hot water extract) | 1/1 | 0.26 |
|  | 1/4 | 0.08 |
|  | 1/16 | 0.07 |
|  | 1/64 | 0.00 |
| Fermented bamboo extract (6) (hot water extraction + ethanol precipitate) | 1/4 | 0.32 |
|  | 1/16 | 0.23 |
|  | 1/64 | 0.36 |
|  | 1/256 | 0.07 |
|  | 1/1024 | 0.04 |
|  | 1/4096 | 0.07 |

The immune functional activities of the fermented bamboo extracts obtained in Example 6 and Example 7 were measured. Dose-response curves shown in FIG. 5 were observed, revealing that the fermented bamboo extracts of the present invention had activity of accelerating natural immunity. Regarding the value of specific activity found from such dose-response curves, the value of the fermented bamboo extract (5) was 7.3 units/mg, and the value of the fermented bamboo extract (6) that had undergone the ethanol precipitate forming step was 230 units/mg (see Table 4). It was revealed by the results that the fermented bamboo extracts obtained by subjecting the fermented bamboo products to hot water extraction had an immunostimulating action, the component having an immunostimulating action was concentrated by ethanol precipitation or could be selectively obtained, and the fermented bamboo extract (6) that had undergone the precipitate forming step exerted an immunostimulating action at a higher level. Furthermore, as shown in Table 4 below, the saccharide content of the fermented bamboo extract (6) was increased to 52 wt %. As described above, specific activity increased, as the saccharide content increased. Accordingly, polysaccharides contained in a fermented bamboo extract are considered to be one of active components having an immunostimulating action.

TABLE 4

| Test sample | Total weight (mg) | Saccharide weight (mg) | Percentage of saccharide (%) | Total activity (units) | Specific activity (units/mg) |
|---|---|---|---|---|---|
| Fermented bamboo extract (5) (autoclaved hot water extract) | 440 | 31 | 7 | 3200 | 7.3 |
| Fermented bamboo extract (6) (hot water extraction + ethanol precipitate) | 27 | 14 | 52 | 6200 | 230 |

Example 9

10. Production of Fermented Bamboo Extract (7)

The fermented bamboo product (1 kg) obtained in Example 1 was added into a reaction reservoir for reflux heating, 10 L of water was poured, and then hot water extraction was performed at 100° C. by heating under reflux. The reaction time was set to 120 minutes. After the completion of reaction, a mixture within the reaction reservoir was filtered to collect about 9 L of a filtrate. The filtrate was concentrated about 10 times, to give a concentrated solution. To the concentrated solution, 95% ethanol was added. Ethanol was added until the ethanol reached a final concentration of 70%. The mixed solution was filtered. The thus formed precipitate was collected and then dried, thereby obtaining a powdery fermented bamboo extract (7).

Example 10

11. Immune Response Test Using Mouse Spleen Cells

Figure 6:
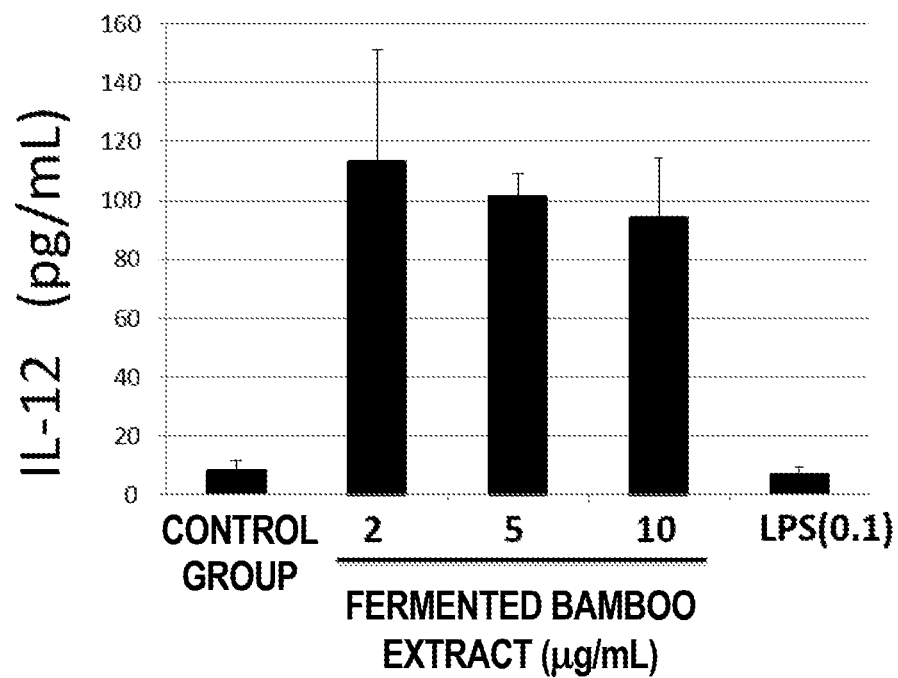
FIG. 6 is a graph showing the results of inducing IL-12 production with the use of a fermented bamboo extract in Example 10.
Figure 7:
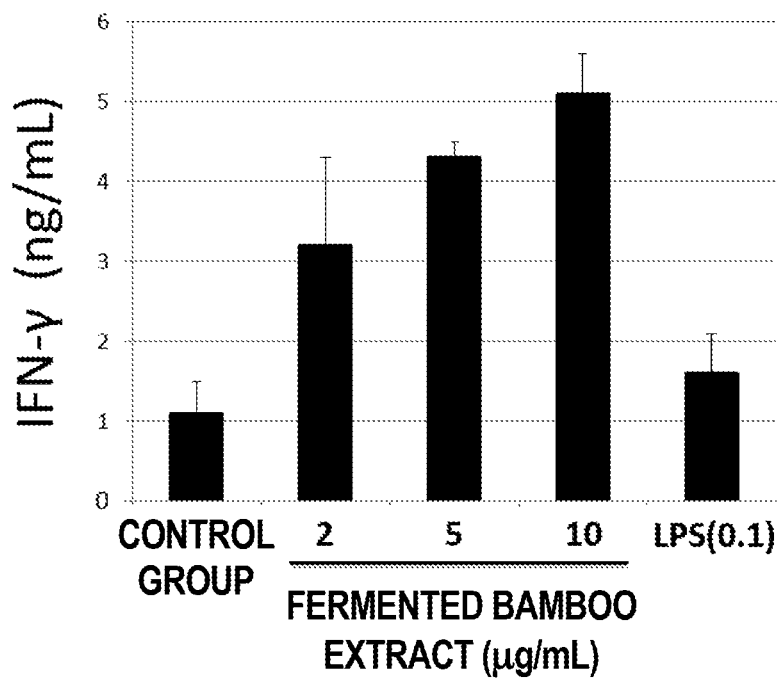
FIG. 7 is a graph showing the results of inducing IFN-γ production with the use of the fermented bamboo extract in Example 10.

Spleen cells were collected from a C57B6 mouse, and then adjusted so that spleen cells were present in an RPMI-1640 liquid medium at $5 \times 10^6$ cells/mL. The fermented bamboo extract (7) produced in Example 9 was used as a test sample. Moreover, since an extract derived from a natural product often contains LPS, whether or not cytokine production by the fermented bamboo extract of the present invention is due to LPS was confirmed using lipopolysaccharide (LPS) as a sample for comparison. The fermented bamboo extract (7) was added to C57B6 mouse spleen cells ($5 \times 10^6$ cells/mL) in such a way as to give final concentrations of 2 µg/mL, 5 µg/mL and 10 µg/mL, and then cells were cultured for 48 hours. Similarly, LPS was added to C57B6 mouse spleen cells ($5 \times 10^6$ cells/mL) in such a way as to give a final concentration of 0.1 µg/mL, and then cells were cultured for 48 hours. After 48 hours of culture, the amounts of IL-12 (p70) and IFN-γ produced in medium were measured by ELISA. The results of the amounts of IL-12 (p70) produced are shown in FIG. 6, and the results of the amounts of IFN-γ produced are shown in FIG. 7. As shown in FIG. 6 and FIG. 7, the fermented bamboo extract of the present invention was revealed to induce IL-12 and IFN-γ production. Furthermore, spleen cells to which LPS had been added were observed to produce neither IL-12 nor IFN-γ, suggesting that cytokine production induced by the fermented bamboo extract of the present invention was not due to LPS, but due to the actions of components other than LPS contained in the fermented bamboo extract.

The present invention is not limited to the above embodiments or Examples. Modes varied by engineering changes may be included in the technical scope of the present invention within the technical idea and the scope of the present invention as disclosed in the attached claims.

INDUSTRIAL APPLICABILITY

The fermented bamboo extract of the present invention is utilized as foods and beverages, and pharmaceutical products, as well as in the livestock or aquaculture fields.

The invention claimed is:

1. A food composition for immunostimulation, comprising, as an active component, a fermented bamboo extract obtained through steps, in this order, of a pulverization step of pulverizing bamboo to obtain bamboo powder, a fermentation step of fermenting the bamboo powder with lactic acid bacteria to obtain a fermented bamboo product, an extraction step of subjecting the fermented bamboo product to hot water extraction to obtain an extract, and a precipitate forming step of adding alcohol to the extract or a concentrated solution thereof to obtain a precipitate.

2. An immunostimulating agent, comprising, as an active component, a fermented bamboo extract obtained through steps, in this order, of a pulverization step of pulverizing bamboo to obtain bamboo powder, a fermentation step of fermenting the bamboo powder with lactic acid bacteria to obtain a fermented bamboo product, an extraction step of subjecting the fermented bamboo product to hot water extraction to obtain an extract, and a precipitate forming step of adding alcohol to the extract or a concentrated solution thereof to obtain a precipitate.

3. A method for producing a fermented bamboo extract, comprising:
- a pulverization step of pulverizing bamboo to obtain bamboo powder;
- a fermentation step of fermenting the bamboo powder with lactic acid bacteria to obtain a fermented bamboo product;
- an extraction step of subjecting the fermented bamboo product to hot water extraction to obtain an extract, and
- a precipitate forming step of adding alcohol to the extract or a concentrated solution thereof to obtain a precipitate.

4. The method for producing a fermented bamboo extract according to claim 1, wherein in the precipitate forming step, the alcohol is added such that the alcohol has a final concentration of 60 wt % to 80 wt %.

5. The method for producing a fermented bamboo extract according to claim 1, wherein in the extraction step, hot water extraction is performed under conditions of 80° C. to 130° C. and 0.1 MPa to 0.3 MPa.

6. The method for producing a fermented bamboo extract according to claim 1, wherein the bamboo is a bamboo stem.

* * * * *